United States Patent
Choi et al.

(10) Patent No.: US 10,695,284 B2
(45) Date of Patent: Jun. 30, 2020

(54) SKIN EXTERNAL COMPOSITION FOR SKIN MOISTURIZATION CONTAINING RED YEAST RICE EXTRACT

(71) Applicant: Amorepacific Corporation, Seoul (KR)

(72) Inventors: Dong Won Choi, Yongin-si (KR); Hong Guen Park, Yongin-si (KR); Han Byul Kim, Yongin-si (KR); Jin Sup Shim, Yongin-si (KR); In Hye Ha, Yongin-si (KR); Youn Joon Kim, Yongin-si (KR); Byung Young Kang, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 243 days.

(21) Appl. No.: 15/848,597

(22) Filed: Dec. 20, 2017

(65) Prior Publication Data

US 2018/0110720 A1    Apr. 26, 2018

Related U.S. Application Data

(62) Division of application No. 14/728,254, filed on Jun. 2, 2015, now Pat. No. 9,877,915.

(30) Foreign Application Priority Data

Jun. 3, 2014   (KR) .................. 10-2014-0067729

(51) Int. Cl.
*A61K 8/97*   (2017.01)
*A61Q 19/00*   (2006.01)

(52) U.S. Cl.
CPC .............. *A61K 8/97* (2013.01); *A61Q 19/007* (2013.01); *A61K 2800/74* (2013.01); *A61K 2800/85* (2013.01)

(58) Field of Classification Search
None
See application file for complete search history.

(56) References Cited

U.S. PATENT DOCUMENTS

| | | | |
|---|---|---|---|
| 2002/0041883 A1 | 4/2002 | Januario et al. | |
| 2011/0165186 A1 | 7/2011 | Wu et al. | |

*Primary Examiner* — Scott Long
*Assistant Examiner* — Evelyn Y Pyla
(74) *Attorney, Agent, or Firm* — Sughrue Mion, PLLC

(57) ABSTRACT

Disclosed herein is a skin external composition containing a red yeast rice extract. More particularly, disclosed is a skin external composition containing a red yeast rice extract which can increase the production of loricrin in keratinocytes and to strengthen the skin barrier function, thereby exhibiting an excellent effect of improving skin moisturization.

11 Claims, 1 Drawing Sheet

SKIN EXTERNAL COMPOSITION FOR SKIN MOISTURIZATION CONTAINING RED YEAST RICE EXTRACT

CROSS-REFERENCE TO RELATED APPLICATIONS

This application is a Divisional of U.S. application Ser. No. 14/728,254 filed Jun. 2, 2015, which claims priority of Korean Application No. 10-2014-0067729 filed Jun. 3, 2014, the disclosures of which are incorporated herein by reference in their entireties.

BACKGROUND OF THE INVENTION

Field of the Invention

The present invention relates to a skin external composition containing a red yeast rice extract, and more particularly, to a skin external composition containing a red yeast rice extract which can increase the production of loricrin in keratinocytes to promote keratinization and to strengthen the skin barrier function, thereby exhibiting an excellent effect of improving skin moisturization.

Description of the Prior Art

The type of keratin that is expressed in keratinocytes is specific depending on the degree of differentiation of keratinocytes. Specifically, the K5/K14 keratin pair is expressed mainly in keratinocytes of the basal layer, and the K10/K1 keratin pair starts to be expressed in place of the K5/K14 keratin pair when keratinocytes migrate from the basal layer to the spinous layer. Loricrin is a protein that is expressed during the final differentiation of keratinocytes. It is required for forming stable keratin by differentiation of keratinocytes, and accounts for 70-85% of the mass of keratin. It has a domain that is rich in glutamine and lysine, which can participate in interpeptide cross-linking which is catalyzed by transglutaminase. In addition, it promotes the cross-linking between keratinocytes, thereby playing an important role in keratinization. Such loricrin binds to the cell membrane in the granular layer to form a protein, and thus is used as a marker in tracking the differentiation of keratinocytes.

Thus, in order to form the horny layer so as to strengthen the skin barrier that prevents the loss of water from skin tissue while promoting the retention of water in skin tissue to thereby prevent skin aging and protect the skin from external environmental changes such as atmospheric drying, UV light and various pollutants, the development of a skin moisturizing substance that promotes the expression of loricrin is required.

PRIOR ART DOCUMENTS

Patent Documents

Patent Document 1: Korean Patent No. 10-119398 (registration date: Oct. 17, 2012).

SUMMARY OF THE INVENTION

Accordingly, the present inventors have found that a red yeast rice extract among natural extracts can strengthen the skin barrier function by increasing the expression of loricrin in keratinocytes, thereby completing the present invention.

Therefore, it is an object of the present invention to provide a skin external composition containing a red yeast rice extract that can improve skin moisturization.

To achieve the above object, the present invention provides a skin external composition for skin moisturization, which contains a red yeast rice extract.

DETAILED DESCRIPTION OF THE INVENTION

Figure 1:
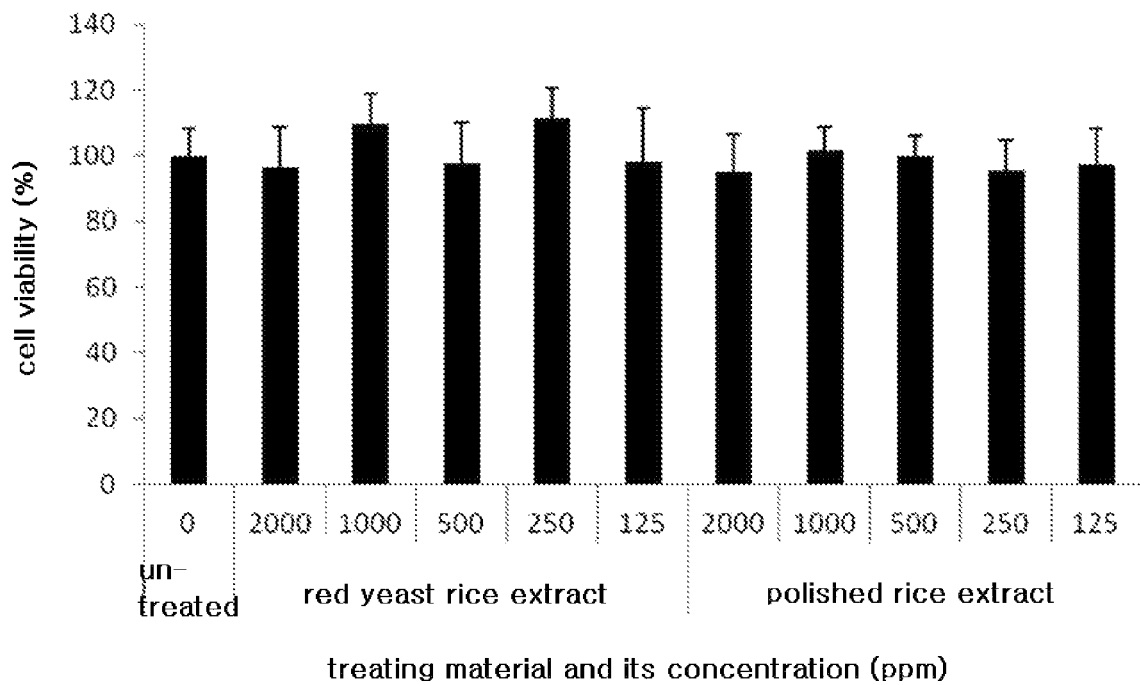
FIG. 1 is a graph showing the effect of a red yeast rice extract on cell proliferation.

The skin external composition according to the present invention contains a red yeast rice extract as an active ingredient.

Red yeast rice is red rice made by fermenting polished rice with the genus *Monascus* (e.g., *Monascus pilosus*) for 15-30 days. In the fermentation process, the red natural pigment monacolin-K is produced, which contains gamma-aminobutyric acid (GABA) as a main component and exhibits various effects, including brain function activation, adult disease prevention, promotion of brain development, cholesterol removal, amelioration and prevention of diabetes, blood pressure lowering, etc.

As used herein, the term "red yeast rice extract" is intended to include not only an extract from red extract rice obtained by fermenting rice with the genus *Monascus* (e.g., *Monascus pilosus*), but also a concentrate obtained by concentrating part or all of the extract, and an infusion, decoction, tincture and fluid extract obtained by drying the concentrate, as well as active ingredients contained in the red yeast rice, and also the red yeast rice itself.

The red yeast rice extract that is used in the present invention can be prepared by any known method. For example, the red yeast rice extract can be prepared by extracting rice yeast rice with water or an organic solvent under reflux, separating the extracted rice into residue and a filtrate by filter-cloth filtration and centrifugation, and concentrating the separated filtrate under reduced pressure. An organic solvent that may be used in the present invention may be selected from among ethanol, methanol, butanol, ether, ethyl acetate, chloroform, butylene glycol, etc., and mixed solvents of these organic solvents and water. In view of the stability of the raw material, a mixed solvent of water and butylene glycol (6:4 w/w) is preferably used. Herein, the extraction is preferably performed at a temperature of 5 to 100° C. for 1-8 hours. If the extraction temperature and time are out of the above ranges, the extraction efficiency can decrease, or a change in the components of the red yeast rice can occur. The extract obtained using the solvent as described above may be macerated, heated and filtered according to a conventional method known in the art to obtain a liquid material. In addition, the extract may also be evaporated to remove the solvent, spray-dried or freeze-dried.

The skin external composition according to the present invention may contain the red yeast rice extract in an amount of 0.001-20 wt %, preferably 0.01-5 wt %, and more preferably 0.1-3 wt %, based on the total weight of the composition. If the content of the red yeast rice extract in the composition is less than 0.001 wt %, the efficacy and effect of the extract will be insignificant, and if the content is more than 20 wt %, there will be a problem in terms of skin safety or formulation.

The composition of the present invention may be used as a skin external composition for skin moisturization, which can increase the expression of loricrin to induce the differentiation of skin keratinocytes to thereby strengthen the skin barrier function. Thus, the composition of the present invention can be effectively used as a skin external composition for preventing or ameliorating dry skin, atopic dermatitis, contact dermatitis or psoriasis, which results from imperfect epidermal differentiation.

The composition according to the present invention may be formulated as a cosmetic composition or a pharmaceutical composition, but is not limited thereto.

The composition according to the present invention may contain a cosmetically and dermatologically acceptable medium or base. The composition may be formulated as a preparation for local application. Examples of formulations for local application include a solution, a gel, a solid, a paste, an emulsion prepared by dispersing an oil phase in a water phase, a suspension, a microemulsion, microcapsules, microgranules, ionic (liposome) and non-ionic vesicles, cream, skin lotion, an ointment, powder, a spray, and a conceal stick. Also, the composition according to the present invention can be formulated as a foam composition or an aerosol composition further containing a compressed propellant. In addition, the composition of the present invention can be formulated according to a conventional method known in the art.

Further, the composition according to the present invention may contain additives which are generally used in the cosmetic field or the dermatology field, for example, a fatty substance, an organic solvent, a solubilizing agent, a thickener, a gelling agent, a softener, an antioxidant, a suspending agent, a stabilizer, a foaming agent, an aromatic, a surfactant, water, an ionic or non-ionic emulsifying agent, a filler, a sequestering agent, a chelating agent, a preservative, vitamins, a blocker, a moisturizing agent, essential oil, a dye, a pigment, a hydrophilic or hydrophobic activator, a lipid vesicle, or other components which are generally used in cosmetics. These additives are contained in amounts which are generally used in the cosmetic field or the dermatology field.

In addition, the composition according to the present invention may further contain a skin absorption-promoting material in order to increase the effect of improving skin moisturization.

Hereinafter, the present invention will be described in further detail with reference to test examples and formulation examples. It is to be understood, however, that these test examples and formulation examples are for illustrative purposes and are not intended to limit the scope of the present invention.

Example 1: Preparation of Red Yeast Rice Extract

To prepare a red yeast rice extract, *Monascus purpureus* (KCTC 6120) was used as a strain. To prepare red yeast rice, polished rice was soaked in water at a weight ratio of 1:1 for hour, and the *Monascus purpureus* strain ($10^6$ CFU/ml) was inoculated into 100 g of the sterilized polished rice and stationary-cultured under aerobic conditions at 30° C. for 2 days and at 25° C. for 6 days. Next, the rice was heated at 90° C. for 20 minutes, and then dried at 50° C. to a water content of 10% or less. The dried rice was ground with a grinder (food mixer FM-707T, Hanil, Seoul, Korea) to prepare red yeast rice powder. A 10-fold weight of a mixture of water and butylene glycol (6:4 (w/w)) was added to the prepared red yeast rice powder, which was then extracted three times at 80° C. and filtered, thereby obtaining a red yeast rice extract (83% yield).

Comparative Example 1: Preparation of Polished Rice Extract 100 g of polished rice was ground with a grinder (food mixer FM-707T, Hanil, Seoul, Korea) to prepare polished rice powder. A 10-fold weight of a mixture of water and butylene glycol (6:4 (w/w)) was added to the prepared rice powder, which was then extracted three times at 80° C. and filtered, thereby obtaining a polished rice extract (84% yield).

Test Example 1: Evaluation of Cytotoxicity

In order to determine the concentration of the red yeast rice extract for treating keratinocytes (purchased from Invitrogen), the viability of the cells was measured.

Specifically, keratinocytes were seeded in a 96-well plate at a density of $1.0 \times 10^4$ cells/well and cultured overnight. The cells were treated with varying concentrations (125, 250, 500, 1000 and 2000 ppm) of the red yeast rice extract of Example 1 and cultured again for 24 hours. For comparison, the cells were treated with varying concentrations (125, 250, 500, 1000 and 2000 ppm) of the polished rice extract of Comparative Example 1 or treated with neither the red yeast rice extract not the polished rice extract, and then cultured for 24 hours. After culture, the medium was removed, and the cells were washed with PBS, after which 0.1 mg/ml MTT (thiazolyl blue tetrazolium blue, Sigma) solution was added to the cells which were then cultured at 37° C. for 2 hours. Then, the added MTT solution was removed, and the purple precipitate was dissolved in DMSO (dimethyl sulfoxide, Sigma Aldrich), after which the absorbance of the solution at a wavelength of 560 nm was measured using a BioTek Synergy 2 spectrophotometer, thereby evaluating the effect of the extract on the proliferation of the cells. The results of the measurement are shown in FIG. 1.

As shown in FIG. 1, it was found that the red yeast rice extract of Example 1 and the polished rice extract of Comparative Example 1 showed no cytotoxicity at a concentration of 2000 ppm or less. However, it was judged that the use of the red yeast rice extract at a concentration of 1000 ppm or less is safe for cells, and thus the red yeast rice extract was used at a concentration of 1000 ppm or less in a subsequent test.

Test Example 2: Analysis of Differentiation Marker Expression (qPCR)

Loricrin is a protein required for forming stable keratin by differentiation of keratinocytes. The horny (keratin) layer is the outermost layer of the skin and functions as a skin barrier that protects the skin from external pollutants and that retains moisture in the skin. Thus, in order to confirm the effect of the red yeast rice extract on the strengthening of the skin barrier function, a change in the expression of loricrin mRNA was analyzed by qPCR.

Specifically, keratinocytes were treated with varying concentrations (125, 250, 500 and 1000 ppm) of the red yeast rice extract of Example 1, and then harvested after 5 days. For comparison, keratinocytes were treated with varying concentrations (125, 250, 500 and 1000 ppm) of the polished rice extract of Comparative Example 1 or treated with neither the red yeast rice extract nor the polished rice extract, and then harvested after 5 days. RNA was extracted from the cultured keratinocytes using a RNeasy mini-kit (QIAGEN), and then synthesized into cDNA using a SuperScript reverse transcriptase III kit (Invitrogen). For gene comparison, 7500 Fast Real-Time PCR was performed using 2× TAQMAN™ universal PCR mix (10 μl), 20× TAQMAN™ expression assay mix (1 μl), cDNA (50 ng) and primers (Loricrin, Hs01894962_s1*).

Figure 2:
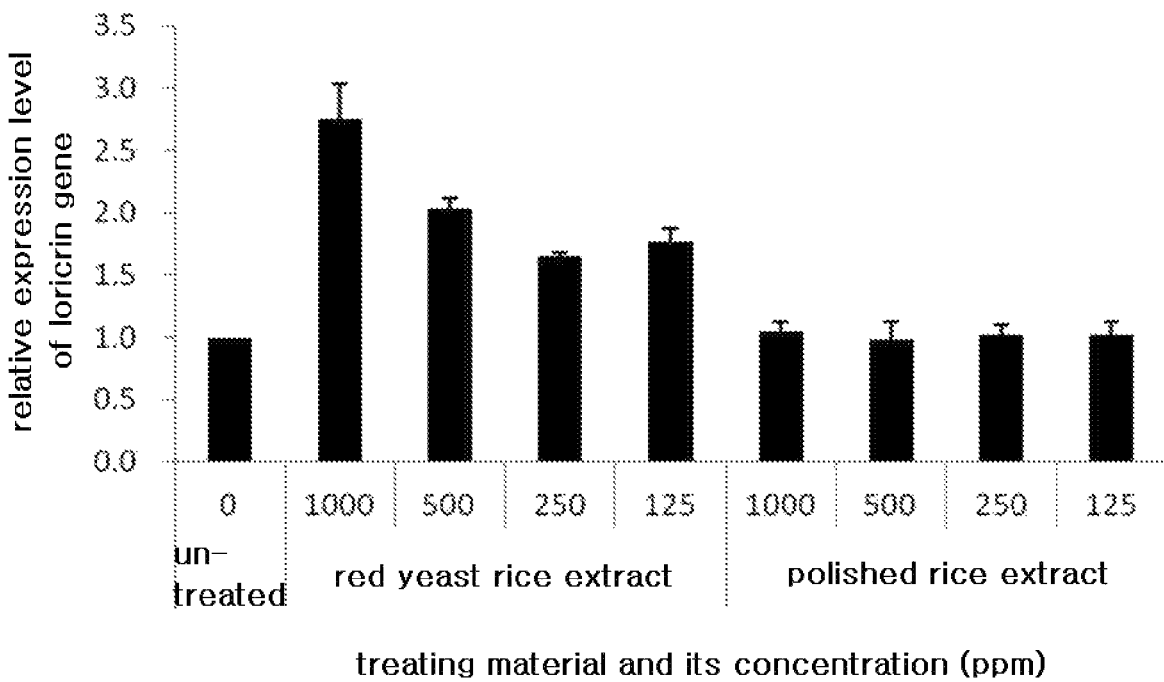
FIG. 2 shows the results of measuring the effect of a red yeast rice extract on a change in the expression of loricrin mRNA by qPCR.

The expression level of the loricrin gene in the cells treated with the red yeast rice extract of Example 1 or Comparative Example 1 was calculated relative to that in the untreated cells (1.0), and the results of the calculation are shown in FIG. 2.

As can be seen in FIG. 2, when keratinocytes were treated with the polished rice extract, the mRNA expression level of loricrin that is one of keratinocyte differentiation markers did not substantially increase, but when keratinocytes were treated with the red yeast rice extract, the mRNA expression level of loricrin significantly increased.

Reference Example 1: Preparation of Formulation 1 and Comparative Formulations 1 and 2

According to the composition shown in Table 1 below, nourishing cream was prepared by a conventional method (unit: wt %).

TABLE 1

| Components | Formulation 1 | Comparative formulation 1 | Comparative formulation 2 |
| --- | --- | --- | --- |
| Purified water | To 100 | To 100 | To 100 |
| Red yeast rice extract (Example 1) | 0.1 | — | — |
| Polished rice extract (Comparative Example 1) | — | 0.1 | — |
| Vegetable hydrogenated oil | 1.50 | 1.50 | 1.50 |
| Stearic acid | 0.60 | 0.60 | 0.60 |
| Glycerol stearate | 1.00 | 1.00 | 1.00 |
| Stearyl alcohol | 2.00 | 2.00 | 2.00 |
| Polyglyceryl-10 pentastearate & behenyl alcohol & sodium stearoyl lactate | 1.00 | 1.00 | 1.00 |
| Arachidyl behenyl alcohol & arachidyl glucoside | 1.00 | 1.00 | 1.00 |
| Cetearyl alcohol & cetearyl glucoside | 2.00 | 2.00 | 2.00 |
| PEG-100 stearate & glycerol oleate & propylene glycol | 1.50 | 1.50 | 1.50 |
| Caprylic/capric triglyceride | 11.00 | 11.00 | 11.00 |
| Cyclomethicone | 6.00 | 6.00 | 6.00 |
| Preservative and fragrance | q.s. | q.s. | q.s. |
| Triethanolamine | 0.1 | 0.1 | 0.1 |

Test Example 3: Measurement of Effect on Increase in Skin Moisturization

In order to measure the effect of the red yeast rice extract on an increase in skin moisturization, evaluation was performed in the following manner using formulation 1 and comparative formulations 1 and 2.

Thirty 40-59-year-old men and women having dry skin were divided into three groups which each consisted of 10 persons and which were to be treated with formulation 1 and comparative formulations 1 and 2, respectively, and the nourishing cream of each of formulation 1 and comparative formulations 1 and 2 was added to the face twice a day for 4 weeks. Before the start of application and at 1, 2 and 4 weeks after the start of application and at 2 weeks after the stop of application (a total of 6 weeks), the moisture content of the skin was measured using Corneometer CM 825 (C+K Electronic GmbH, Germany) under constant temperature and constant humidity conditions (24° C. and 40% relative humidity). The results of the measurement are shown in Table 2 below. The results in Table 2 are expressed as percent increases in the Corneometer value after certain periods relative to the value measured immediately the start of application of the nourishing cream.

TABLE 2

| | Percent increase in moisture content | | | |
| --- | --- | --- | --- | --- |
| Test groups | After 1 week | After 2 weeks | After 4 weeks | After 6 weeks |
| Formulation 1 | 45 | 43 | 47 | 23 |
| Comparative formulation 1 | 35 | 38 | 37 | 18 |
| Comparative formulation 2 | 30 | 32 | 32 | 15 |

As can be seen from the results in Table 2 above, in the case in which comparative formulation 2 was applied, a percent increase in moisture content of about 32% was observed up to 4 weeks after the start of application, but after the application of comparative formulation 2 was stopped, the percent increase in the moisture content decreased to 15%. In the case in which comparative formulation 1 containing the polished rice content was applied, a percent increase in moisture content of about 37% was observed up to about 4 weeks, but after the application of comparative formulation 1 was stopped, the percent increase in the moisture content greatly decreased to 18%. However, in the case in which formulation 1 containing the red yeast rice extract was applied, a percent increase in moisture content of about 47% was observed up to 4 weeks, and after the application of formulation 1 was stopped, the skin moisture decreased, but was maintained at a high level. This suggests that the composition of the present invention, which contains the red yeast rice extract, has an excellent effect of moisturizing the skin.

Test Example 4: Measurement of Effect on Restoration of Skin Barrier Function

To measure the effect of the red yeast rice extract on the restoration of skin barrier function reduced by skin injury, a test was performed in the following manner. The skin barrier of the upper arm of each of 10 adult men and women was damaged by a tape stripping method, and each of formulation 2 and comparative formulations 3 and 4, prepared according to the composition shown in Table 3 below, was applied to the upper arm while the transdermal water loss (TEWL) was measured using Vapometer (Delfin, Finland) once a day for 7 days. Herein, comparative formulation 4 was used as a negative control vehicle. The results of the test are shown in Table 4 below. The results in Table 4 are expressed as percent changes in TEWL after treatment with the formulation relative to before treatment with the formulation.

TABLE 3

| Components | Formulation 2 | Comparative formulation 3 | Comparative formulation 4 |
|---|---|---|---|
| Purified water | 69 | 69 | 70 |
| Propylene glycol | 30 | 30 | 30 |
| Example 1 | 1 | — | — |
| Comparative Example 1 | — | 1 | — |

TABLE 4

| Test groups | Percent change in TEWL | | | | | | |
|---|---|---|---|---|---|---|---|
| | Before treatment | Day 1 | Day 2 | Day 3 | Day 4 | Day 5 | Day 6 |
| Formulation 2 | 100 | 111.3 | 110.7 | 88.1 | 60.5 | 42.7 | 23.2 |
| Comparative formulation 3 | 100 | 119.4 | 112.7 | 92.5 | 68.4 | 57.3 | 39.5 |
| Comparative formulation 4 | 100 | 121.4 | 112.7 | 98.3 | 70.5 | 62.3 | 43.5 |

As can be seen from the results in Table 4, in the case in which the skin was treated with the red yeast rice extract, the transdermal water loss (TEWL) was quickly returned to the normal level, and the skin barrier damage was recovered.

As described above, the composition of the present invention, which contains the red yeast rice extract, strengthens the skin barrier function, thereby exhibiting an excellent effect of improving skin moisturization.

What is claimed is:

1. A skin external composition for skin moisturization, which contains a red yeast rice extract as an active ingredient, wherein the red yeast rice extract is obtained by adding a mixture of butylene glycol and water to a prepared red yeast rice using a weight ratio of the water and the butylene glycol of 6:4, and conducting an extraction at a temperature of 80° C. to 100° C.

2. The skin external composition of claim 1, wherein the composition comprises the red yeast rice extract in an amount of 0.001-20 wt % based on the total weight of the composition.

3. The skin external composition of claim 1, which is for increasing expression of loricrin in keratinocytes.

4. The skin external composition of claim 1, which is for strengthening skin barrier.

5. The skin external composition of claim 1, wherein the red yeast rice extract is prepared by extraction at a temperature of 80° C. for 1-8 hours.

6. The skin external composition of claim 1, which is for moisturizing a skin of a subject who has a condition selected from the group consisting of dry skin, atopic dermatitis, contact dermatitis, and psoriasis.

7. The skin external composition of claim 1, wherein the composition further comprises a cosmetically acceptable additive and/or a dermatologically acceptable additive.

8. The skin external composition of claim 1, wherein the composition further comprises a skin-absorption-promoting material.

9. The skin external composition of claim 1, wherein the red yeast rice is obtained by fermenting polished rice with a yeast under aerobic condition.

10. The skin external composition of claim 9, wherein the yeast is *Monascus purpureus* strain.

11. The skin external composition of claim 1, which is for improving differentiation of skin keratinocytes.

* * * * *